United States Patent [19]

Kanewske, III.

[11] Patent Number: 4,948,563
[45] Date of Patent: Aug. 14, 1990

[54] WASTE CONTAINER INSERT FOR WASHING AUTOMATED IMMUNOASSAY APPARATUS PROBE

[75] Inventor: William J. Kanewske, III., Dallas, Tex.

[73] Assignee: Abbott Laboratories, Abbott Park, Ill.

[21] Appl. No.: 352,661

[22] Filed: May 9, 1989

Related U.S. Application Data

[63] Continuation of Ser. No. 47,832, May 8, 1987, abandoned.

[51] Int. Cl.$^5$ .................. B01L 3/00; G01N 35/00
[52] U.S. Cl. .......................... 422/99; 422/63; 436/49; 134/182; 134/184; 134/198; 134/201
[58] Field of Search ........................... 422/63–65, 422/99–100; 436/49; 134/182–183, 198, 201

[56] References Cited

U.S. PATENT DOCUMENTS

| | | |
|---|---|---|
| 4,076,503 | 2/1978 | Atwood et al. . |
| 4,111,051 | 9/1978 | Tamm et al. . |
| 4,131,426 | 12/1978 | Range . |
| 4,265,855 | 5/1981 | Mandle et al. . |
| 4,341,568 | 7/1982 | Christensen . |
| 4,456,037 | 6/1984 | Gocho . |
| 4,495,149 | 1/1985 | Iwata et al. . |
| 4,510,251 | 4/1985 | Kirkemo et al. . |
| 4,528,158 | 7/1985 | Gilles et al. . |
| 4,543,238 | 9/1985 | Mimura et al. . |
| 4,730,631 | 3/1988 | Schwartz . |

FOREIGN PATENT DOCUMENTS

| | | | |
|---|---|---|---|
| 2819-820 | 5/1977 | Fed. Rep. of Germany | ...... 356/246 |
| 2049179A | 12/1980 | United Kingdom . | |

Primary Examiner—Robert J. Warden
Assistant Examiner—Lyle Alfandary-Alexander
Attorney, Agent, or Firm—Clifford A. Dean; Roberta L. Hastreiter

[57] ABSTRACT

An article for washing automated immunoassay apparatus probe is provided in the form of a plug member with first and second chambers. The first chamber is defined by a inner wall and a bottom surface which when positioned below a probe of a clinical analysis apparatus provides for recirculation of liquid dispensed from the probe back along the outer surface of the probe to remove residual sample from the probe surface prior to conducting subsequent tests with the probe. In the preferred embodiment of the plug, the second chamber is provided with a plurality of passages for drainage of fluid to a reagent waste container which, in the preferred embodiment, incorporates the plug member at the orifice thereof.

18 Claims, 2 Drawing Sheets

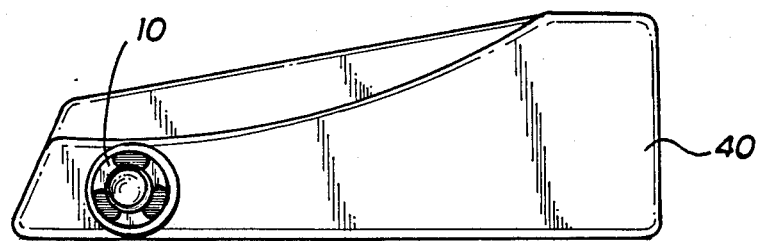
FIG. 6
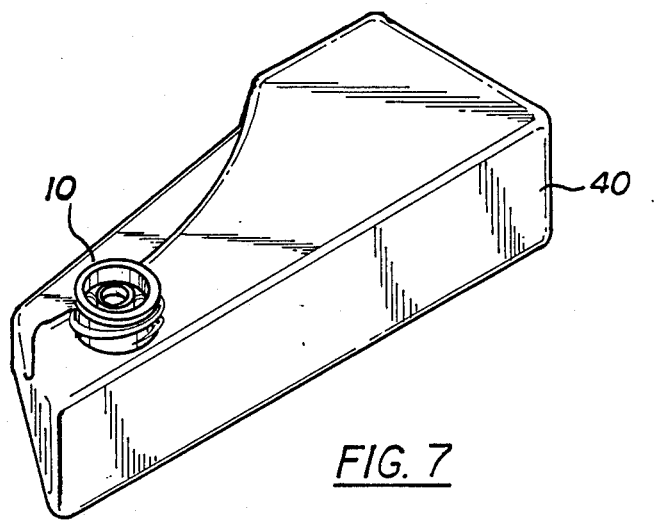
FIG. 7
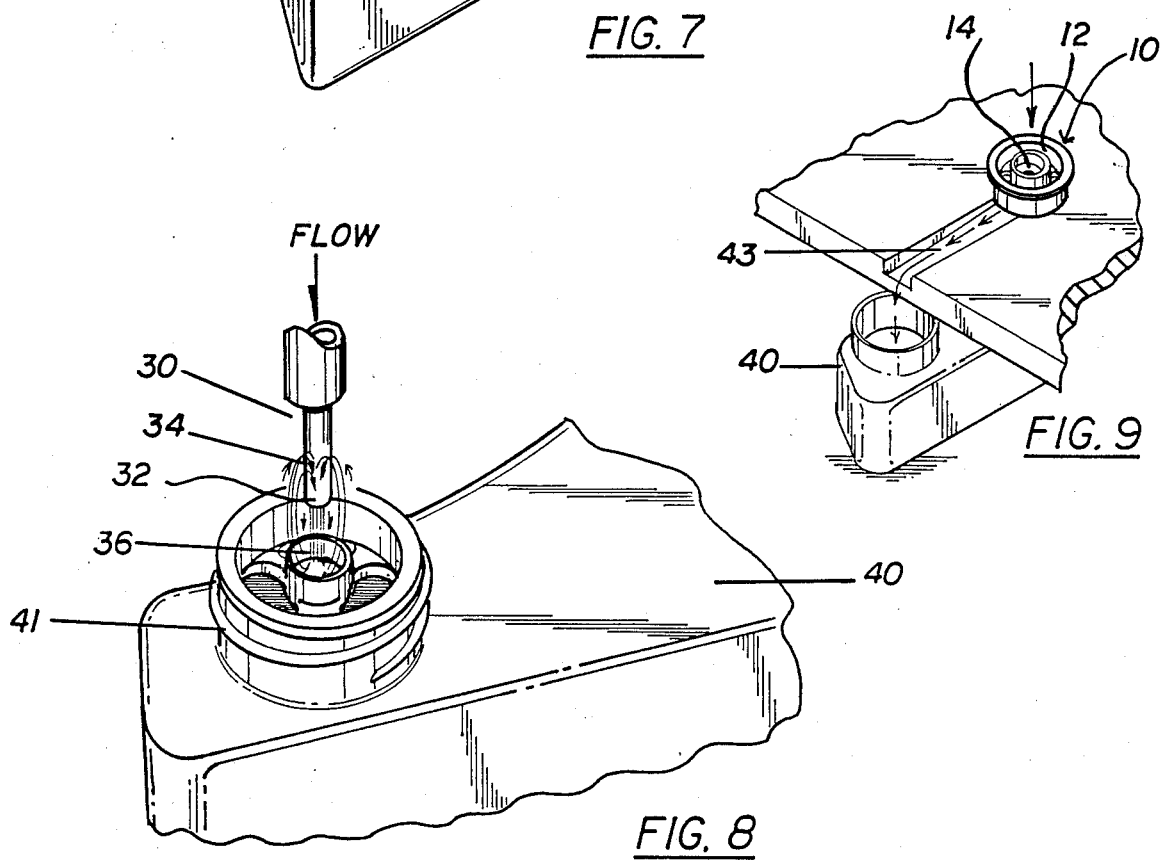
FIG. 9
FIG. 8

WASTE CONTAINER INSERT FOR WASHING AUTOMATED IMMUNOASSAY APPARATUS PROBE

This application is a continuation of application Ser. No. 047,832, filed May 8, 1987.

TECHNICAL FIELD

The present invention relates to a waste container orifice insert used to facilitate washing of the outer surface of a dispensing means, such as a probe between individual sample tests conducted on an automated diagnostic assay apparatus. More particularly, the present invention relates to a plug member adapted to receive and redirect pressurized fluid discharged by the probe to the outer surface of the probe, thereby removing sample carryover. The plug also provides for drainage of the redirected solution into a waste container.

BACKGROUND OF THE INVENTION

A variety of automated liquid assay apparatuses for conducting assays of various liquids, especially biological fluids, for substances contained therein are known. Two such apparatuses are the TDx ® Analyzer and ADx ™ Analyzer available from Abbott Laboratories, Abbott Park, Ill. The $TD_x$ ® and $AD_x$ ™ analyzers are automated diagnostic assay instruments generally used to measure analyte concentrations in biological fluids such as serum, plasma, and whole blood. The ADx ™ is specifically designed to conduct automated assays for drug of abuse analytes such as amphetamine/methamphetamine, cocaine, THC, morphine, heroin or the like. The TDx ® analyzer has been previously described in other patents, commonly assigned herewith, such as U.S. Pat. No. 4,510,251 to Kirkemo et al.

The TDx ® and ADx ™ analyzers, for example, provide capabilities for both fluorescence polarization and nephelometric analysis, as well as for other systems of analysis. Whatever assay system is employed in a TDx ® or ADx ™ Analyzer, as in other instruments of the prior art, the assays are carried out by well-known techniques which involved dispensing reagents from bulk containers located remotely from the test samples undergoing analysis, mixing the reagents with the samples in reaction cuvettes while the latter are indexed, by means of a carrier, comprising a rotating carousel, or the like, from one analysis station to another. Subsequent to delivery of all reaction components to a cuvette, a wash or buffer solution is normally passed through the probe to eliminate any residual reaction components prior to subsequent tests. Typically, the wash solution is passed through the probe and dispensed to a remotely positioned waste container. While this internal cleansing of the probe is generally satisfactory, it does not provide for washing of the outer surface of the probe which can retain residual sample in certain assays.

Sample material retained on the probe surface is especially troublesome in automated analyzers where failure to adequately wash the outer surface of the dispensing probe can cause undesired sample carryover to subsequent tests. When the analyte or substance to be detected is a drug of abuse such as cocaine, THC, amphetamine/methamphetamine, morphine, heroin, or the like, preventing sample carryover is crucial to maintenance of sample integrity.

Accordingly, there is a need for an article which provides for effective washing or cleansing of the reaction component dispensing means of an automated liquid assay apparatus to eliminate the sample carryover and improve the performance of assays using readily available analytical instrumentation.

SUMMARY OF THE INVENTION

The present invention comprises an article for use in a clinical analysis apparatus of the type before described, which is useful to facilitate removal of the sample carryover from dispensing means such as a probe. Specifically, the invention relates to a plug member having a continuous outer wall and an inner wall. The inner wall of the plug defines an outer barrier of a first chamber having a first bottom surface which is inclined downwardly towards its center. The inner wall also defines an inner barrier of a second chamber having a second annular bottom surface, an outer barrier defined by the outer wall, and at least one drainage port through the bottom surface. The outer wall projects outwardly away from the second bottom surface in an upward direction to a first top edge. The inner wall projects outwardly away from the first bottom surface in an upward direction and terminates at a second top edge. The first bottom surface is recessed from or spaced below the second top edge to provide a pool for liquids discharged from fluid dispensing means, such as a probe to be cleansed positioned adjacent to and above the first chamber. Pressurized wash fluid discharged into the first chamber from the probe during cleansing of the interior thereof is redirected outwardly by the inclined bottom surface and upwardly along the inner wall and away from or beyond the second top edge, thereby providing fluid circulation about the outer surface of the adjacently positioned dispensing means or, in other words, cleansing engagement with the exterior of the probe through a "shower effect".

In the preferred embodiment, the plug member is substantially circular with coaxially aligned continuous inner and outer walls. Further, means for mounting and/or securing the plug in a orifice or inlet port of a waste container is provided. The preferred securement means include a plurality of legs extending downwardly away from the second bottom surface. The legs include free ends having flanged portions projecting laterally outwardly with respect to the outer wall. The preferred plug member is also provided along the first top edge with a laterally outwardly projecting flange which forms an outer lip designed to cooperate with the upper rim of a waste container.

The preferred embodiment of the present invention is adapted to securely cooperate with the opening of a waste container and provides a number of previously unseen advantages when positioned therein. Specifically, the plug facilitates effective washing of an automated clinical analysis apparatus of a probe in a simple and inexpensive manner. Use of a plug member of the type described by the present invention in an automated clinical analysis apparatus minimizes sample carryover without modifications to the hardware or construction of the analyzer.

Further objects and advantages attained by the invention will be best understood by studying the following detailed description of a preferred embodiment together with the drawings.

BRIEF DESCRIPTION OF THE DRAWINGS

FIG. 6 is a top view showing the plug member of the present invention positioned within a waste container.

FIG. 7 is a perspective view showing the plug member of the present invention positioned within a waste container.

FIG. 8 is a representation of probe surface washing as accomplished with a waste container incorporating the plug member of the present invention.

FIG. 9 shows an alternate embodiment of the present invention.

DETAILED DESCRIPTION OF THE INVENTION

Figure 1:
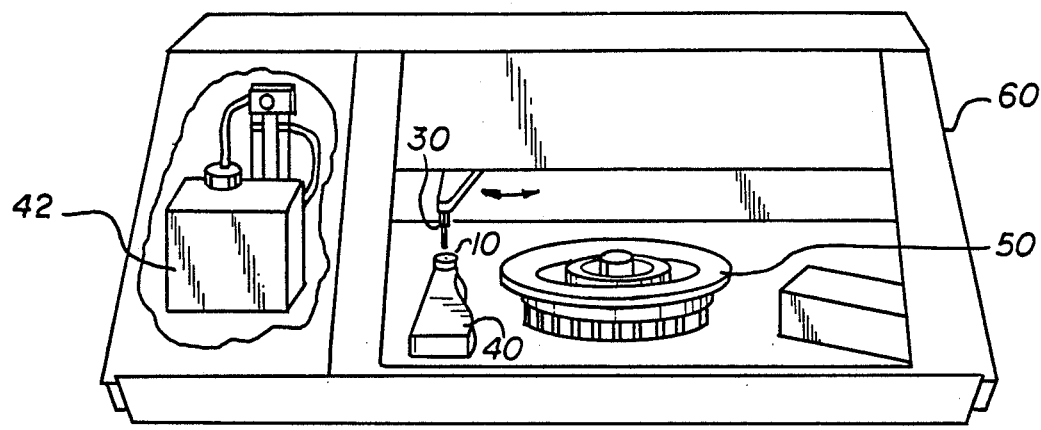
FIG. 1 is perspective view of a clinical analysis apparatus showing a waste container incorporating the present invention mounted in a representative position in the analyzer.
Figure 2:
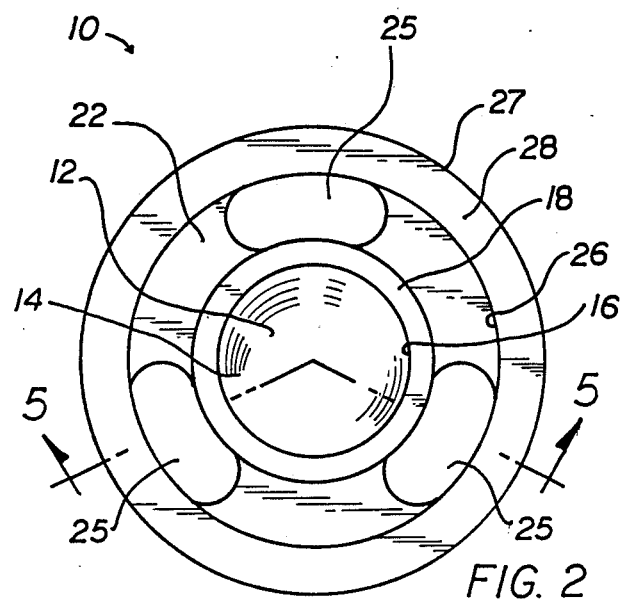
FIG. 2 is a top view of the plug member of the present invention.

Referring now to the drawings, there is shown in FIGS. 2-5 a preferred embodiment of the present invention generally referred to by the reference numeral 10. As illustrated in FIGS. 6 and 7, the preferred embodiment of the present invention cooperatively engages a waste container positioned in a clinical analysis apparatus at a position removed from sample processing (see FIG. 1).

In the preferred embodiment, the plug member 10 has a two chamber configuration defined by a continuous outer wall 26 and an inner wall 16.

In the preferred embodiment, the plug 10 is substantially circular with the outer wall 26 and inner wall 16 coaxially aligned and is adapted to cooperatively engage a container orifice or inlet port. The inner wall 16 defines an outer barrier of a first chamber 12 having a first bottom surface 14 which is inclined downwardly towards its center. The inner wall 16 also defines an inner barrier of a second chamber 22. The second chamber 22 includes a second bottom surface 24 which is annular in configuration. The bottom surface 24 of the second chamber 22 has at least one drainage port therethrough. As seen best in FIGS. 2 and 3, in the preferred embodiment the bottom surface 24 includes three generally equally spaced drainage ports 25.

The outer wall 26 of the second chamber 22 projects outwardly away from the second bottom surface 24 in an upward direction to a first top edge 28. As seen best in FIG. 4, the first top edge 28 extends laterally outwardly beyond the outer wall 26 forming an outer lip 27. When plug 10 cooperatively engages the orifice of container a waste 40, the plug 10 is appropriately positioned in bottle 40 with (as seen in FIGS. 6 and 7) the lip 27 fitting in sealing position with rim 41 of bottle 40.

The inner wall 16 projects outwardly away from the first bottom surface 14 in an upward direction to a second top edge 18. In the preferred embodiment shown, the second top edge 18 is recessed with respect to, or space below, first top edge 28 to assure that liquid overflow from the first chamber 12 is directed into the second chamber 22 and subsequently into waste container 40 rather than spilling over outer wall 26 into the internal environment of the clinical analysis apparatus 60.

An important feature of the plug 10 is that the first bottom surface 14 is recessed from, or spaced below, the second top edge 28 to provide a pool for liquid 36 discharged from fluid dispensing means such as probe 30 positioned thereabove as seen in FIG. 8. When pressurized wash liquid 36 is discharged from probe 30 into first chamber 12 the inclined bottom surface 14 and inner wall 16 redirect the wash liquid 36 outwardly to and upwardly along the inner wall 16 away from or upwardly beyond the top edge 18, thereby providing fluid circulation about the outer surface 34 of the adjacently positioned probe 30 or, in other words, cleansing engagement with the exterior of the probe 30 through a "shower effect" in the manner represented in FIG. 8. The "shower effect" or washing produced when discharged liquid 36 is redirected upwardly along the inner wall 16 to the probe surface 34 is effective to substantially remove any sample remaining on the outer surface 34 of the probe 30. By way of example, the "shower effect" washing of the probe surface 34 is accomplished best when the probe tip 32 is centrally positioned within inner chamber 12, approximately 1/10" below second upper edge 18. This position will result in circulation of fluid over about ⅛" of the surface of the lower portion of probe 34. It will be appreciated that the discharged fluid can be delivered to inner chamber 12 as either a steady stream or as intervaled pulses of short duration.

Figure 3:
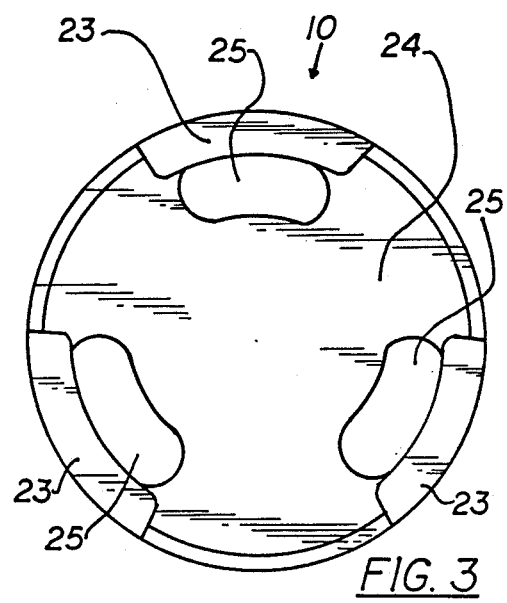
FIG. 3 is a bottom view of the plug member of the present invention.
Figure 4:
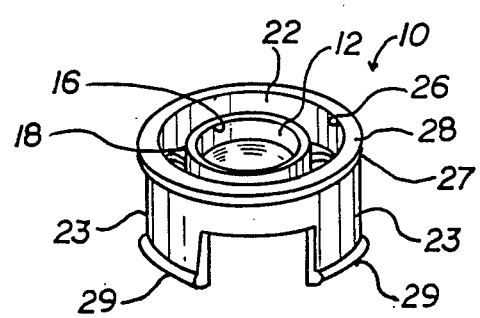
FIG. 4 is a perspective view of the plug member of the present invention.
Figure 5:
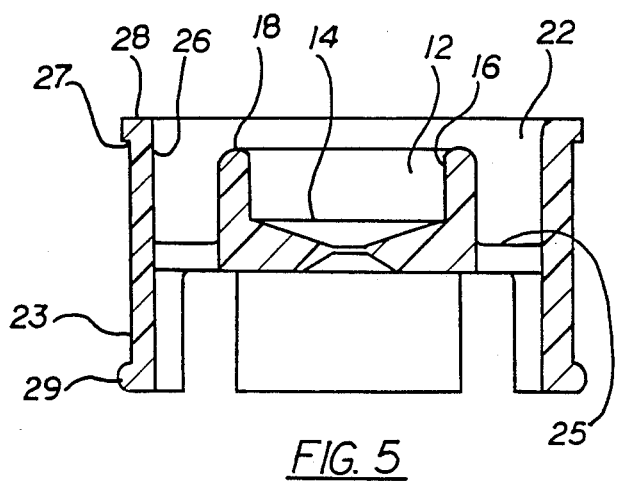
FIG. 5 is a cross sectional view of the plug member of the present invention.

In the preferred embodiment, the plug 10 is secured to a waste bottle 40 by previously discussed lip 27 and a plurality of legs 23 extending downwardly away from the second bottom surface 24. Each leg 23 is provided at its free end with a flange 29 projecting outwardly with respect to outer wall 26. As seen in FIG. 3, the preferred embodiment includes three legs 23 positioned generally equal distance along the second bottom surface 24. Referring to FIGS. 6 and 7, positioning of the preferred embodiment of the plug 10 in a waste container 40 is shown. In the preferred embodiment, the plug 10 and waste container 40 comprise a disposable combination.

The preferred embodiment of the present invention is described herein as a plug insert 10 positioned in the orifice of a waste container 40. However, as shown in FIG. 9, one alternative embodiment, (in which similar parts are represented with prime designations) plug 10' can be positioned external to and in fluid communication with the orifice of a waste container 40'. Fluid communication between the waste container 40' and plug 10' is provided by channel 43. The present invention can also be provided with a drainage aperture through the inclined bottom surface 14 of the inner chamber 12. As seen in FIG. 9, this drainage aperture 15 is preferably located at the center of bottom surface 14 and facilitates drainage of wash solution dispensed to inner chamber 12' by a probe in the manner previously described.

It is to be understood that the plug 10 can be made by a number of processes including lathing and molding and can be made from a number of suitable materials easily ascertained by one of skill in the art. In the preferred embodiment the plug 10 is made of a plastic. While various plastics can be used such as polyethylene, polypropylene or the like, prefereably the plug 10 is polypropylene (90%) and teflon (10%).

Surface 34 cleaning of probe 30 of a clinical analysis apparatus is best seen by the following example using an Abbott ADx ™ Analyzer.

1. An aliquot of unknown sample and pretreatment solution are pipetted into a predilute well positioned on carousel 50. A sufficient volume of diluent buffer from a buffer reservoir 42 is added to the predilute well. Following incubation of the mixture in the predilute well, a sample from the predilute well is pipetted into a reaction cuvette positioned on the carousel 50. A background intensity reading is taken and specified amounts of tracer and antibody and samples from the predilute well are then added to the cuvette, together with sufficient diluent buffer to raise the final volume to that required in the specific assay. Subsequent to delivery of all reagent components to the cuvette, the probe 30 is removed from the site of the sample and reaction cuvette containing carousel 50 and positioned over the waste container bottle 40. When positioned adjacent the waste container bottle 40, diluent buffer 32 is delivered through the probe 30 and the outer surface 34 of the probe is washed in the manner shown in FIG. 8. Specifically, the probe tip 32 is positioned centrally within inner chamber 12 approximately 1/10" below second edge 18. Diluent buffer is delivered through the probe tip 32 at a flow rate between 700 to 900 μm/sec. Delivering diluent buffer through the probe 30 under these conditions produces the "shower effect" washing along about $\frac{1}{8}"\pm 1/100"$ of the probe surface 34 in a manner which effectively removes any sample retained on the surface 34.

It will be appreciated that the discharge pressure needed to produce the "shower effect" type cleaning action of the probe surface 34 will vary depending on distance between the plug 10 and probe tip 32 as well as the specific dimensions of the inner chamber 12. It is to be understood that the present invention is directed to a plug 10 having a configuration which provides for cascading type recirculation of liquids about a probe surface and drainage of such recirculated fluid into a waste container. In this regard, the foregoing detailed description is to be considered as illustrative rather than limiting, since many variations within the scope of the invention which will fully achieve these and other advantages of the invention will be apparent to one of ordinary skill in the art. Accordingly, it is intended that the appended claims, including all equivalents thereof, be construed solely to define the scope of the invention.

What is claimed is:

1. An article for simultaneously cleansing the inner and outer surfaces of an automated centrally bored immunoassay probe after each sample use thereof comprising:

a unitary plug member adapted to be mounted in an inlet port of a waste container and having a continuous upstanding outer wall and a coaxially aligned upstanding inner wall, said inner wall defining an outer barrier of a first chamber having a bottom surface which is inclined downwardly toward its center, said inner wall also defining an inner barrier of a second annular chamber having an annular bottom surface and an outer barrier defined by said outer wall, said first and second chambers being concentrically aligned, and said annular bottom surface of said second chamber having at least one opening formed therein to provide drainage into a waste container upon which said plug member may be mounted, said outer wall projecting upwardly from said annular bottom surface to a first top edge, said inner wall projecting upwardly from said inclined bottom surface to a second top edge, said first chamber being adapted to have a used, centrally bored sample probe generally centered thereover with pressurized wash liquid being directed through said probe to cleanse the inner bore thereof and with said pressurized wash liquid then engaging said inclined bottom surface of said first chamber and being directed upwardly by said inclined bottom surface and the inner surface of said inner wall for cleansing engagement with the outer surface of said used probe, any overflow of wash liquid from said first chamber being over said second top edge into said second annular chamber for draining therefrom through said drainage opening into a waste container.

2. The article of claim 1 wherein said second top edge is space below said first top edge.

3. The article of claim 1 wherein said plug member is substantially circular.

4. The article of claim 1 wherein said first top edge extends laterally outwardly beyond said outer wall forming an outer lip.

5. The article of claim 1 wherein said plug member is made of a plastic.

6. The article of claim 1 wherein said plug member is made of polypropylene and teflon.

7. The article of claim 1 further comprising means thereon for mounting said plug in a waste container inlet port.

8. The article of claim 7 wherein said mounting means comprises a plurality of legs extending downwardly away from said annular bottom surface, said legs terminating at flanged free ends, said flanges projecting laterally outwardly with respect to said outer wall.

9. In combination with a waste container having an inlet port into which wash liquid is directed under pressure from a centrally bored sample probe of an automated immunoassay apparatus after each sample-testing operation of said probe, said probe being positionable above said inlet port with said wash liquid passing therethrough serving to cleanse said bore thereof, a unitary plug member mounted in said waste container inlet port and adapted to provide simultaneous cleansing of the exterior surface of said probe while said probe is positioned thereabove, said plug member comprising continuous and co-axially aligned upstanding inner and outer walls, said inner wall defining an outer barrier of a first cylindrical chamber having a bottom surface which is inclined downwardly toward the center thereof, said inner wall also defining an inner barrier of a second ring-like chamber having an annular bottom surface and an outer barrier defined by said outer wall, said annular bottom surface having at least one drainage port therethrough into said waste container, said first and second chambers being concentrically aligned, said outer wall projecting upwardly from said annular bottom surface to a first top edge, said first top edge extending laterally outwardly away from said outer wall and forming an outer lip which is supported on an upper edge of said inlet port of said waste container, said inner wall projecting upwardly from said inclined bottom surface to a second top edge, the inclined bottom surface and inner wall surface of said first chamber providing simultaneous cleansing of the exterior surface of said probe by redirecting said pressurized wash liquid upwardly from said first chamber for cleansing engagement with said exterior probe surface, and means on said plug member for retaining said plug member in said waste container inlet port.

10. The plug member of claim 9 wherein said second top edge is spaced below said first top edge.

11. The plug member of claim 9 wherein the configuration thereof is substantially circular.

12. The plug member of claim 9 wherein said member is made of a plastic.

13. The plug member of claim 9 wherein said member is made of polyethylene.

14. The plug member of claim 9 wherein said retaining means comprises a plurality of legs extending downwardly from said annular bottom surface, said legs terminating at flanged free ends, said flanges projecting laterally outwardly with respect to said outer wall.

15. The plug member of claim 14 wherein said retaining means comprises three flanged legs.

16. In combination with a waste container having an inlet port into which wash liquid is directed under pressure from a centrally bored sample probe of an automated immunoassay apparatus after each sample-delivery operation of said probe, during which operation said probe is dipped into one of a plurality of different sample containers with an aliquot of said sample then being delivered by said probe to a reaction cuvette for test purposes, said probe then being positionable above said inlet port of said waste container with said wash liquid passing therethrough serving to cleanse said bore thereof prior to delivery of an aliquot of the next sample to a reaction cuvette, a unitary plug member mounted in said inlet port of said waste container to provide simultaneous cleansing of the exterior surface of said probe while said probe is positioned thereabove, said plug member comprising a first open-topped chamber defined by a bottom surface and a first upstanding continuous wall formation, a second open-topped ring-like chamber surrounding said first chamber and defined by a ring-like bottom surface integral with said bottom surface of said first chamber, by said first upstanding continuous wall formation, and by a second upstanding continuous wall formation spaced outwardly of said first wall formation, the configuration of said first chamber being such that the wash liquid discharged from said probe into said first chamber is redirected upwardly therefrom into cleansing engagement with the outer surface of said probe to provide generally simultaneous cleansing of both the inner and outer surfaces of said probe, the height of said first wall formation being less than that of said second wall formation to permit overflow of wash liquid from said first chamber into said second chamber, and at least one drainage opening provided in said ring-like bottom surface of said second chamber to permit drainage of said wash liquid therefrom into said waste container.

17. The plug member of claim 16 wherein the configuration of said first chamber is characterized by a bottom surface which is inclined downwardly toward the center thereof.

18. The plug member of claim 16, wherein mounting means are provided thereon for mounting said plug member in said inlet port of said waste container.

* * * * *